United States Patent [19]

Tomita et al.

[11] Patent Number: 5,543,392
[45] Date of Patent: Aug. 6, 1996

[54] DIGESTIVE TRACT CELL ACTIVATING AGENT OF EGF AND LACTOFERRIN

[75] Inventors: Mamoru Tomita; Seiichi Shimamura, both of Kanagawa; Yasuo Fukuwatari, Kawasaki; Ichizo Shinoda, Kanagawa, all of Japan

[73] Assignee: Morinaga Milk Industry Co., Ltd., Tokyo, Japan

[21] Appl. No.: 374,785

[22] PCT Filed: Feb. 25, 1993

[86] PCT No.: PCT/JP93/00235

§ 371 Date: Apr. 3, 1995

§ 102(e) Date: Apr. 3, 1995

[87] PCT Pub. No.: WO94/03203

PCT Pub. Date: Feb. 17, 1994

[30] Foreign Application Priority Data

Jul. 29, 1992 [JP] Japan .................................. 4-202724

[51] Int. Cl.$^6$ .......................... A61K 38/40; A61K 38/18; A61K 38/14

[52] U.S. Cl. .................... 514/8; 514/6; 514/12; 514/21

[58] Field of Search ................... 514/12, 21, 8, 514/6

[56] References Cited

U.S. PATENT DOCUMENTS

| | | | |
|---|---|---|---|
| 4,820,690 | 4/1989 | Gregory et al. | 514/12 |
| 4,977,137 | 12/1990 | Nichols et al. | 514/6 |
| 5,214,028 | 5/1993 | Tomita et al. | 514/6 |

*Primary Examiner*—Howard E. Schain
*Attorney, Agent, or Firm*—Wenderoth, Lind & Ponack

[57] ABSTRACT

The present invention provides an activating agent of digestive tract cells, which contains an epidermal growth factor, lactoferrins, a hydrolysate of the lactoferrins, or a mixture thereof.

The activating agent of digestive tract cells of the present invention has such effects as prevention and improvement of a damage to the digestive tract, improvement of digestive tract functions deteriorating with age, and acceleration of growth and proliferation of digestive tract cells of a newborn. It is also possible to add it to, or mixed with, various food products to obtain digestive tract cels activating foods.

9 Claims, 4 Drawing Sheets

DIGESTIVE TRACT CELL ACTIVATING AGENT OF EGF AND LACTOFERRIN

TECHNICAL FIELD

The present invention relates to a digestive tract cell activating agent. More particularly, the present invention relates to a digestive tract cell activating agent which contains an epidermal growth factor, lactoferrins and/or a hydrolysate of lactoferrin, and is useful widely in the medical treatment area including prevention and therapy of digestive tract diseases, promotion of digestive tract functions and activation thereof.

BACKGROUND ART

The Epidermal growth factor (hereinafter sometimes referred to as "EGF") is a peptide having a molecular weight of about 6,000, has proliferation-stimulating function for a wide variety of mammalian cells, and is contained in body fluid of all mammals. Since EGF is contained in breastmilk in a relatively high concentration, general attention is attracted by the relationship between EGF and growth and development of a newborn (neonate in the case of an animal), and among others, the effect of EGF on the development of digestive tract of neonatal rat and mouse has been studied. For example, it has been clarified that feeding a neonatal rat with an artificil milk added with EGF accelerate synthesis of DNA in the small intestine [C. L. Berseth: American Journal of Physiology, Vol. 253, p. G662, 1987], and that it increases the wet weight of stomach [J. Falconer: Biology of the Neonate, Vol. 52, p. 347, 1987, and E. V. O'Loughlin, et al: American Journal of Physiology, Vol. 249, p. G674, 1985]. It has also been demonstrated that administration of EGF to a neonatal rat accelerates development functions of the small intestine and mucosa thereof [C. Malo, et al: Gastroenterology, Vol. 83, p. 23, 1982, and Y. Oka, et al: Endocrinology, Vol. 112, p. 940, 1983].

There are known some cases of application of EGF for therapy of digestive tract diseases in accordance with the findings as described above. A recent case is reported where administration of EGF to an eight month old infant suffering from necrotic inflammation of small intestine (necrotinsing enteritis) led to recovery of fataldamages to the digestive tract [P. E. Sullivan, et al: Lancet, Vol. 338, p. 53, 1991], demonstrating clinical effectiveness of EGF.

The effect and the action mechanism of EGF on cultured cells have widely been studied to date since discovery of EGF in 1962. Regarding digestive tract cells, it has now been clarified that DNA synthesis in intestine apithelial cells is accelerated by EGF, and this action is caused via an EGF receptor presentin the cytoplasmic membrane [M. E. Forgue Lafite, et al: FEBS Letter, Vol. 114, p. 243, 1980; and N. Gallo-payet, et al: Endocrinology, Vol. 116, p. 194, 1985].

Sice usefulness of EGF for activating the digestive trtact has been revealed, blending of EGF into powder milk for infant was proposed (Japanese Patent Provisional Publication No. 62-228,225; and Japanese Patent Provisional Publication No. 1-148,146). More specifically, because digestive tract cells are not matured, a newborn is susceptible to easy entry of various bacteria and antigens through the digestive tract, and furthermore because of an incomplete immunological function, a newborn is sensible to infectious diseases. Therefore, with a view to promoting growth or proliferation of digestive tract cells, accelerating development of the digestive tract functions, and preventing ingression of bacteria, it was proposed to blend EGF into powder milk for infant.

Breastmilk contains, in addition to EGF, other substances showing proliferation stimulating function. Lactoferrin (hereinafter sometimes referred to as "Lf") is an iron-binding protein having a molecular weight of about 80,000 contained in a very large quantity in breastmilk, and has been known to exhibit an antimicrobial activity against detrimental micro-organisms such as *Escherichia coli, candida, clostridium* and Staphylococcus [Journal of Pediatrics, Vol. 91, p. 1, 1979; and Journal of Dairy Science, Vol. 67, p. 60, 1981]. The known functions of Lf and its hydrolysate thereof include antimicrobial activity and inhibition of tyrosinase activity (European Patent Provisional Publication No. 438,750); prevention of adherence of pathogen (Japanese Patent Provisional Publication No. 3-220,130); and antiviral activity (Japanese Patent Provisional Publication No. 1 233,266). More recently, it has been clarified that DNA synthesis of rat small intestine epithelial crypt cells is accelerated by Lf [B. L. Nichols, et al: Pediatric Research, Vol. 21, p. 563, 1987], and Lf is attracting the general attention as a new proliferation stimulating factor in breastmilk. From the same point of view as that of EGF, blending of Lf to an infant food composition is also proposed (Japanese Patent Provisional Publication No. 1-93,534).

As described above, EGF and Lf have so far been used singly in powdery milk for infant and infant food compositions. The number of persons suffering from digestive tract diseases such as gastric ulcer is on the other hand increasing under the effect of mental stress and it is needless to mention that elderly persons of advanced age tend to have decreased functions of digestive tract. Under such circumstances, it is considered significant to effectively utilize the results of research on the above mentioned powdery milk for infant and the like for prevention and therapy of digestive tract diseases of adults and for activating digestive tract cells functionally becoming poorer with age.

Unlike digestive tract cells of a newborn or an infant in the midst of growth, single administration of EGF or Lf cannot bring about a remarkable effect for digestive tract cells of an adult because the cells of an adult have already discontinued the rapid proliferation or the rapid growth which is observed in the case of newborn or an infant. In order to use EGF or Lf for the above mentioned purpose, it is necessary to intensify activity thereof by some method or other. Such a method has not however been known conventionally, and no attempt has as yet been made to try simultaneous use of EGF and Lf. Simultaneous use of EGF and Lf has not been tried since synergistic effect could not be expected from the simultaneous use because of the difference in action mechanism as a cell proliferation stimulating factor (for example, Japanese Patent Provisional Publication No. 1-93,534).

DISCLOSURE OF INVENTION

The present inventors carried out studies on biological activity of lactoferrin, apolactoferrin, metal saturated or partially metal-saturated lactoferrin and mixtures thereof (hereinafter, these may be collectively referred to as "lactoferrins") and hydrolysates of the lactoferrins, and as a result, obtained the following novel facts which have not conventionally been known:

(1) While protein containing lactoferrins usually loses biological activity when hydrolyzed, a hydrolysate of lactoferrin group retains the cell proliferation function of lactoferrin, exerts synergistic action with EGF, and has thus strong growth or proliferation accelerating functions of digestive tract cells.

(2) Lactoferins exert synergistic effect with EGF and provide stronger growth or proliferation accelerating functions of digestive tract cells than in single use of lactoferrin or EGF.

The present invention was developed on the basis of the above-mentioned findings and has an object to provide an activating agent of digestive tract cells, which accelerates recovery of digestive tract of a person having a damaged digestive tract or subjected to an operation of digestive tract as a result of ulcer, activates digestive tract cells of which the function has become poorer along with aging of an aged, and accelerates growth or proliferation of digestive tract cells of a newborn to promote development of the digestive tract itself.

To achieve the above-mentioned object, the present invention provides an activating agent of digestive tract cells, which contains an epidermal growth factor, lactoferrins, a hydrolysate of the lactoferrins, or a mixture thereof.

In a preferred embodiment, the activating agent in digestive tract cells in the present invention, the effective dose of administration of the above mentioned lactoferrins, a hydrolysate of lactoferrins, or a mixture thereof should preferably be within a range of from 1 to 500 mg/kg of body weigt per day for an adult, and the effective dose of administration of the epidermal growth factor should preferably be within a range of from 0.01 to 50 μm/kg of body weight per day for an adult (man).

The activating agent of digestive tract cells of the present invention has such effects as prevention and improvement of a damage to the digestive tract, improvement of digestive tract functions deteriorating with age, and acceleration of growth and proliferation of digestive tract cells of a newborn. It is also possible to add it to, or mixed with, various food products to obtain digestive tract cells activating foods.

BRIEF DESCRIPTION OF DRAWINGS

FIG. 1 shows the relationship between the concentration of added bovine lactoferrin (bLf) and the quantity of incorporated 3H-thymidine, in which the ordinate represents the quantity of incorporated 3H-thymidine, and the abscissa, the concentration of added bLf. In FIG. 1, the marks ○ and ● respectively indicate bLf single (n=1) and coexistence with EGF (n=1). FIG. 2 illustrates the relationship between the concentration of added pepsin hydrolysate of bovine lactoferrin (bLf-μy) and the quantity of incorporated $^3$H-thymidine: the ordinate represents the quantity of incorporated $^3$H-thymidine, and the abscissa represents the concentration of added bLf Hy. In FIG. 2, the marks ○ and ● respectively indicate bLf-Hy single (n–4) and coexistence with EGF (n=4).

FIG. 3 illustrates the effect of bovine lactoferrin (bLf) on proliferation of small intestine epithelial cells of rat in he presence of mouse EGF, and FIG. 4 illustrates the effect of pepsin hydrolysate of bovine lactoferrin (bf-Hy) on proliferation of the small intestine epithelial cells of rat in the presence of mouse EGF. In FIG. 3, the marks Δ, ▲, ○ and ● respectively indicate the control group (group with no addition; n–6), the EGF-added group (n–6), the bLf-added group (n=6) and EGF/bLf-added group (n=6). In FIG. 4, the marks Δ, ▲, ○ and ● respectively indicate the control group (group with no addition; n–6), the EGF added group (n–6), the bLf Hy-added group (n=6) and EGF/bLf-Hy-added group (n=6).

BEST MODE FOR CARRYING OUT THE INVENTION

Figure 1:
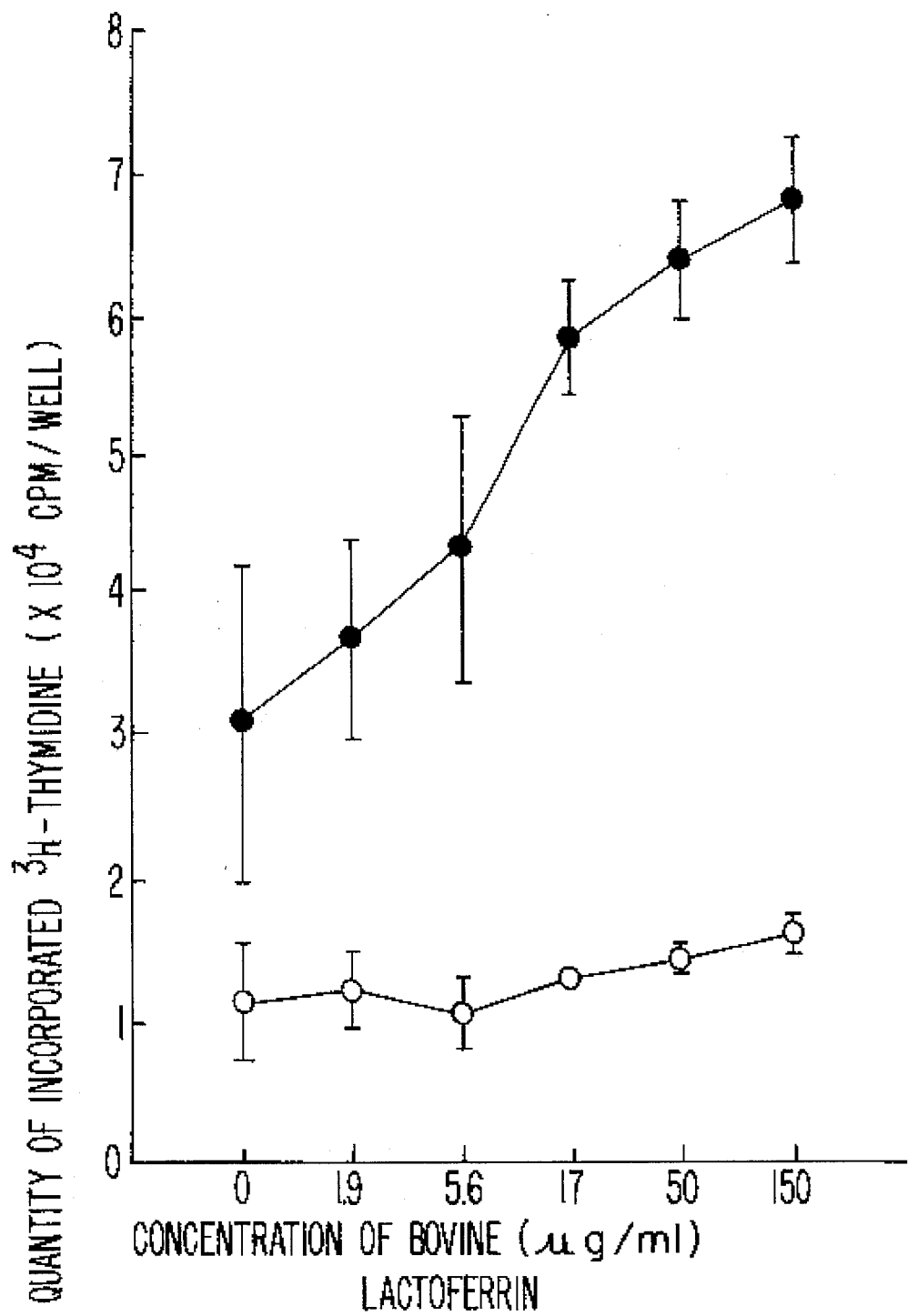
FIGS. 1 to 4 illustrate the results of tests carried out to investigate the effects of the activating agent of digestive tract cells in the present invention.

Lactoferrins used in the present invention may be any of commercially available Lf, Lf separated from animal milk or human milk by any conventional method, apo lactoferrin available by de-ironization of lactoferrin by an conventional method, metal-saturated or partially metal-saturated lactoferrin available by chelation of apo-lactoferrin with a metal such as iron, copper, zinc and manganese, or a mixture thereof.

The hydrolysate of lactoferrins used in the present invention may be a product available by hydrolyzing the above-mentioned lactoferrins with the use of an acid or anenzyme by any conventional method, a product available by refining such a hydrolysate by any conventional method, or a mixture thereof. The above mentioned lactoferrins and the hydrolysate of the lactoferrins may be used in mixture, and as is clear from the Tests described later, a hydrolysate of lactoferrins is recognized to have synergetic effect with EGF.

EGF used in the present invention may be any of EGF isolated from human urine, animal milk or human milk by any conventional method, EGF manufactured by DNA recombination technique, chemically synthesized EGF, commercially available EGF and a mixture thereof.

The digestive tract cells activating agent in the present invention is applicable as a medical drug, or may be used by adding to, or mixing with, foods or the like. When used as a medical drug, it may be used by appropriately mixing with an excipient, a volume increasing agent, or a diluent in any of such forms as tablets, pills, powder, capsules, and suppository.

The dose of administration of EGF, an effective ingredient of the digestive tract cells activating agent in the present invention, lactoferrins and/or hydrolysate of the lactoferrin in, varying with the age, body weight and condition of the subject (human), should preferably be within a range of from 1 to 500 mg/kg per day for lactoferrins and/or hydrolysate of the lactoferrins, and within a range of from 0.01 to 50 μm/kg for EGF.

When applying the digestive tract cells activating agent in the present invention for foods, it may be appropriately added in a required quantity to a liquid diet, an enteral feeding, a modified milk powder, etc. It is of course very effective to add lactoferrins, a hydrolysate of lactoferrins, and EGF to a food originally not containing these ingredients.

Since lactoferrins, a hydrolysate of the lactoferrins and EGF are natural products present in milk, it is needless to mention that these ingredients pose no safety problem.

Now, the functions and the effects of the present invention is described below in detail by showing Test Examples.

TEST 1

This test was carried out to determine an optimum concentration for DNA synthesis acceleration activity of EGF relative to small intestine epithelial cells.

(1) Preparation of Sample

Commercially available mouse submaxillary gland originating EGF (manufactured by Takara Shuzo Company) was used.

(2) Procedure

IEC18 cells (purchased from the American Type Culture Collection) which are epithelial crypt-cells of rat small intestine were inoculated into a 24-well culture plate by 10,000 cells per hole and cultured with Dulbecco modified Eagle's medium containing 10% fetal bovine serum (hereinafter abbreviated as "10% FBS-DMEM") until the cells became confluence (1 ml of medium was used per well). Then, the medium was replaced with 1% FBS-DMEM culture was conducted for another three days to introduce the cell cycle into the resting phase. The medium was replaced with of 1% FBS-DMEM (0.5 ml) containing EGF at various concentrations and culture was conducted for 18 hours. Then, the medium was replaced with DME (0.35 ml) containing $^3$H-thymidine (tritium labeling: thymidine 1 micro curie/ml), the cultuure was conducted for another two hours. The result cells were rinsed twice with phosphate-buffered saline [PBS (−), 2 ml], then, ice-cooled 5% trifluoroacetic acid (5% TFA, 2 ml) was added. This was stored in a refrigerator for an hour. The cells were washed twice with 5% TFA (2 ml) and 1N NaOH (0.4 ml) was added. By holding this at 37° C. for an hour, the cells were dissolved. Then, the solution was neutralized by adding 6N HCl (0.08 ml), and therefore, the quantity of $^3$H-thymidine incorporated into DNA was measured by means of a liquid scintillation counter.

(3) Results

The results of this test are shown in Table 1. As is clear from Table 1, the optimum working concentration of EGF for DNA synthesis of these cells was revealed to be 10 ng/ml. Thereafter, therefore, EGF was used at a concentration of 10 ng/ml.

TABLE 1

| Quantity of incorporated $^3$H thymidine | EGF concentration (ng/ml) | | | | | |
|---|---|---|---|---|---|---|
| (cpm) | 0 | 0.08 | 0.4 | 0.2 | 10.0 | 50.0 |
| Average value (n = 4) | 5783 | 17874 | 19644 | 25398 | 26152 | 22665 |
| Standard deviation | 2153 | 1253 | 926 | 1196 | 1675 | 1297 |

Test 2

This test was carried out to investigate the effects of simultaneous use of Lf and EGF or simultaneous use of a hydrolysate of Lf (Lf Hy) and EGF on DNA synthesis of 1EC18 cells.

(1) Preparation of Sample

Commercially available mouse submaxillary gland originating EGF (manufactured by Takara Shuzo Company) and bovine lactoferrin (bLf) (manufactured by Yukijirushi Nyugyo Company) were used.

The bLf-Hy was prepared from bLf as follows. Commercially available bLf (manufactured by Olefina Company) was dissolved in purified water at a ratio of 500 g/9.5 l; pH of the resultant solution was adjusted to 3.0 by adding 1M (mol/l) hydrochloric acid; then, commercially available porcine pepsin (manufactured by Sigma Company) was added at a ratio of 10 g per 500 g bLf; and hydrolysis was carried out at 37° C. for six hours. Then, pH was adjusted with 6N sodium hydroxide; enzyme was deactivated by heating at 80° C. for ten minutes; the solution was cooled to the room temperature and subjected to Celite filtration; the filtrate was frozen and dried to obtain bLf Hy.

(2) Procedure

A test was carried out in the same manner as in the Test 1. The test samples included samples added with bLf or bLf Hy at various concentrations, and those added with EGF in an amount of 10 ng/ml and bLf or bLf-Hy at various concentrations.

(3) Results

Figure 2:
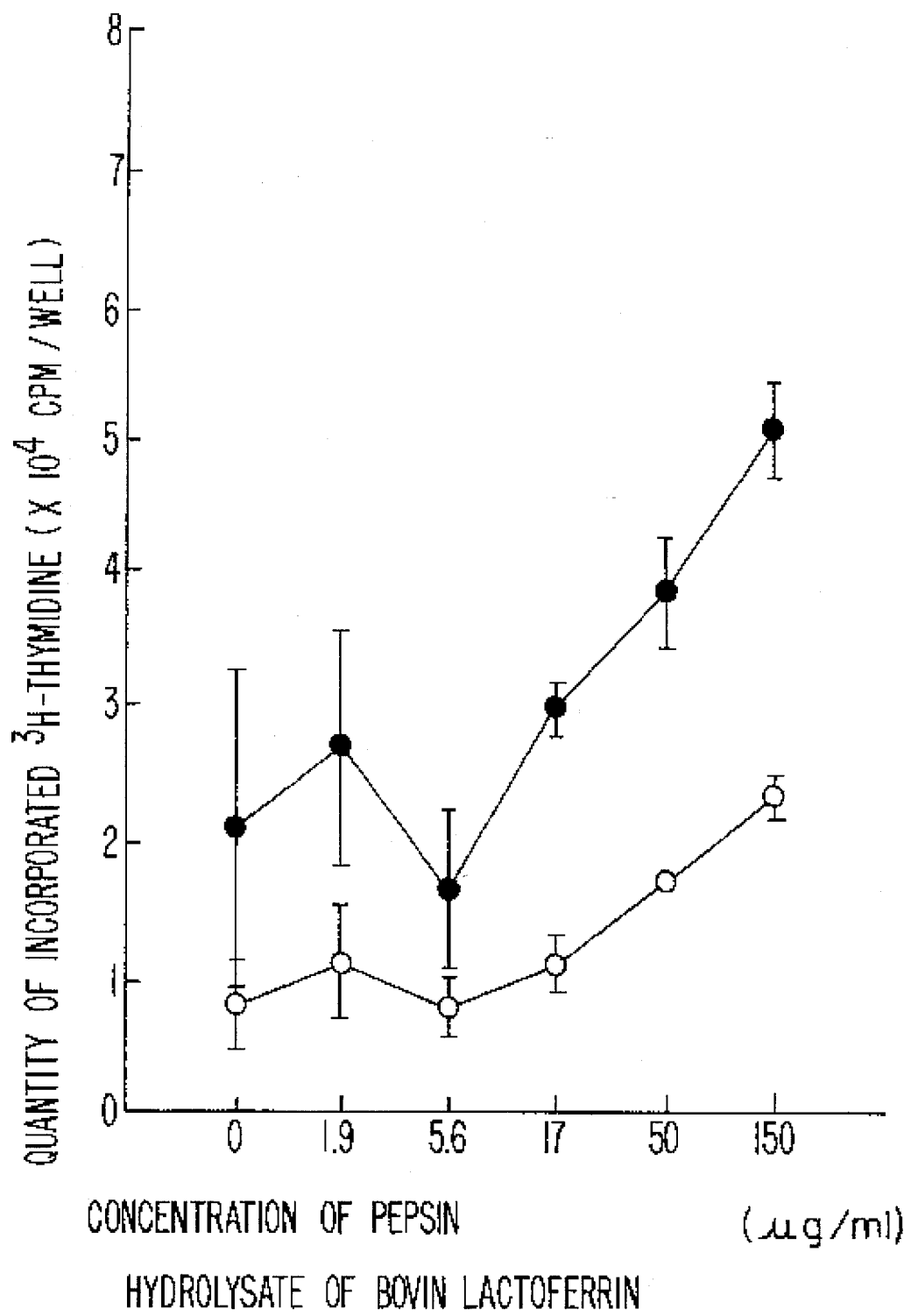

The results of this test are shown in FIGS. 1 and 2.

As is clear from FIG. 1, no effect was observed in single use of bLf, whereas, in coexistence of EGF, a remarkable increase in the quantity of incorporated 3H-thymidine into DNA of IEC18 cells was observed at a bLf concentration of from 17 to 150 µg/ml, and a synergic effect of EGF and bLf on DNA synthesis was demonstrated.

As is evident from FIG. 2, furthermore, an effect of single use of bLf-Hy was observed at bLf-Hy concentrations of 50 and 150 µg/ml. In the presence of EGF, the quantity of incorporated 3H-thymidine increased more remarkably than in single use of bLf-Hy at bLf-Hy concentrations of 50 and 150 µg/ml, thus demonstrating a synergic effect of bLf-Hy and EGF on DNA synthesis. Tests carried out by changing kinds of bLf and Lf Hy gave almost the same results.

Test 3

Since the Test 2 revealed a particularly remarkable acceleration of the quantity of incorporated $^3$H-thymidine into DNA of IEC18 cell by the simultaneous use of EGF and bLf or EGF and bLf-Hy, this test was carried out to investigate whether or not this fact was actually reflected in the final cell activation, i.e., whether or not it had an effect on proliferation of cells.

(1) Preparation of Sample

The same EGF, bLf and Lf Hy as in the Test Example 2 were employed.

(2) Procedure

ICE18 cells (the same ones as in the Test 1) were inoculated onto a 24-well culture plate by 5,000 cells per well, and were cultured for ten days with 1% FBS DMEM (0.5 ml) containing the following test subjects. During this test period, the medium was replaced on the third and the sixth days, and the number of cells was measured on the third, the sixth and the tenth days. The number of cells was counted by a hemocytometer after treating the cells with 0.25% trypsin solution and suspending them in the solution.

The test subjects included a sample added with nothing, a sample added with 10 ng/ml EGF, a sample added with 50 µg/ml bLf or bLf-Hy, and a sample added with 10 ng/ml EGF and 50 µg/ml bLf or bLf-Hy.

(3) Results

Figure 3:
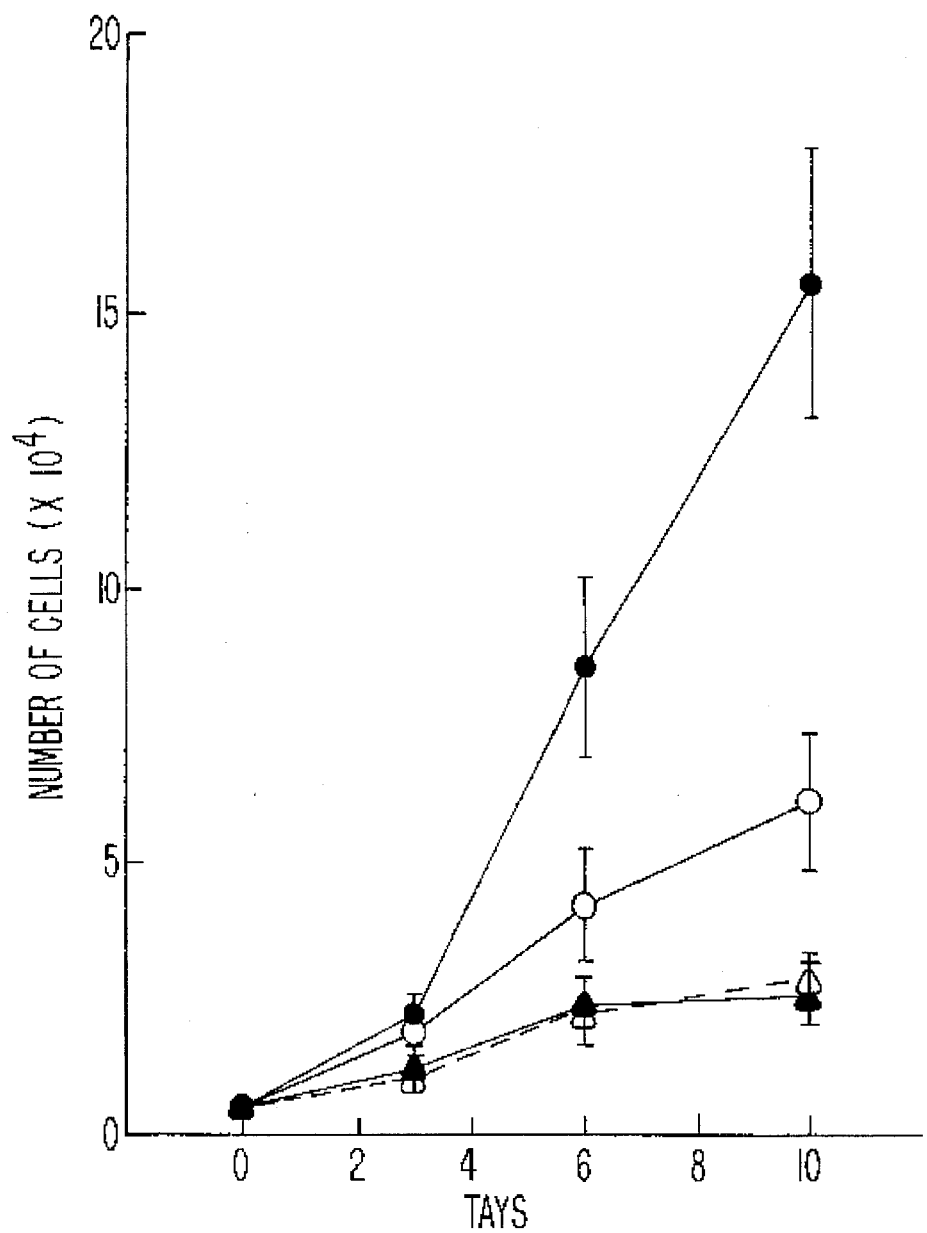
Figure 4:
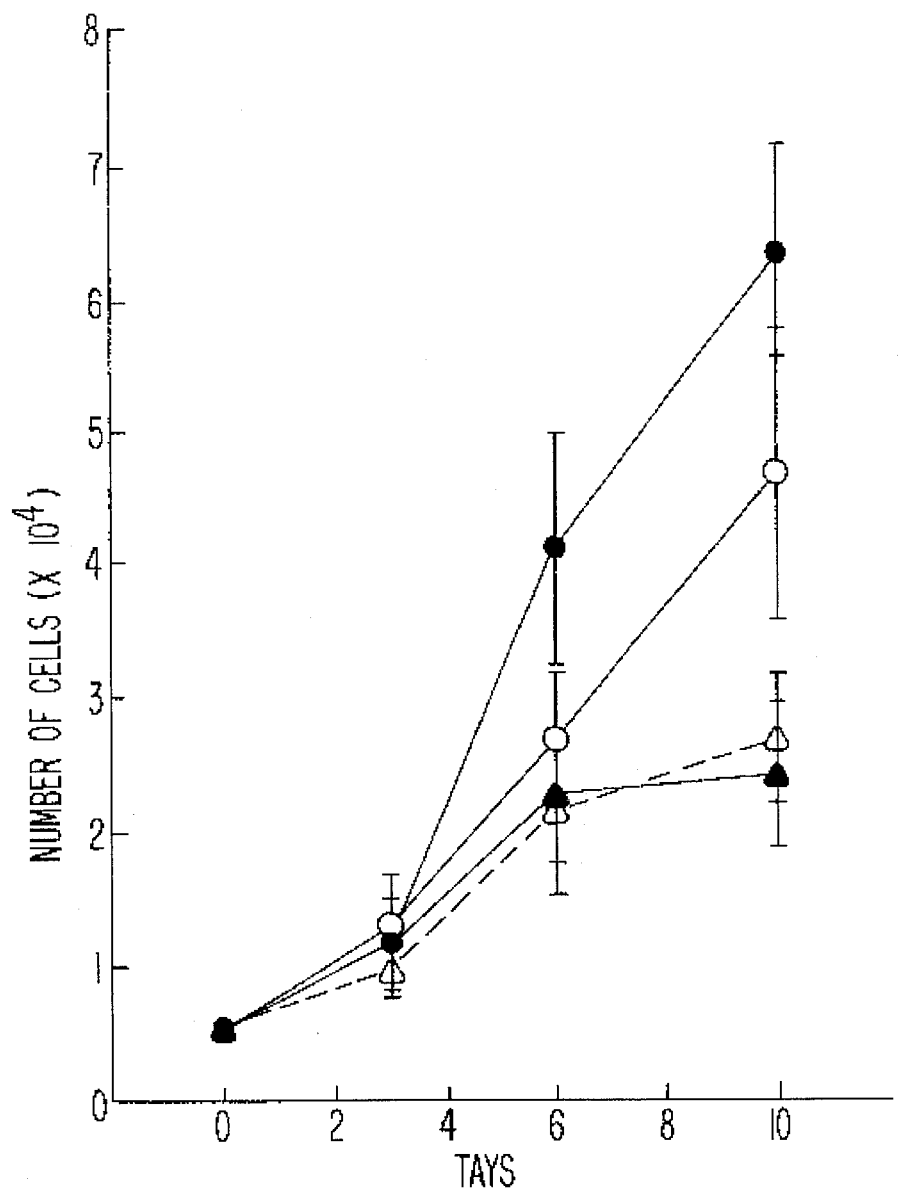

The results of this test are shown in FIGS. 3 and 4.

As is clear from FIGS. 3 and 4, the number of cells of the group of single addition of EGF (▲) increased at almost the same rate as in the control group (Δ) with no addition, clearly showing absence of effect in EGF single addition. For the group with addition of EGF and bLf shown in FIG. 3 (●). The remarkable increase in cell numbers was observed on the sixth and the tenth days of culture. Similarly, for the group with addition of EGF and bLf-Hy-shown in FIG. 4 (●), the number of cells increased on the with and the tenth days of culture. The results for the group with single addition of bLf shown in FIG. 3 (○) and the group with single addition of bLf-Hy shown in FIG. 4 (○) reveal an effect poorer than those of the group with simultaneous addition of EGF, but the number of cells significantly increased on the sixth and the tenth days of culture as compared with the control group (Δ) and the group with single addition of EGF (▲). A test was carried out with different kinds of Lf and Lf-Hy provided almost the same results.

Now, the present invention is described below further in detail by means of Examples. The present invention is not however limited to these Examples.

Various kinds of lactoferrin and EGF used in the individual Examples were prepared as shown in the References described below.

Reference Example 1 (Preparation of Apo-lactoferrin)

Apo-lactoferrin was prepared as follows from commercially available bovine lactoferrin (manufactured by Oleofina Company) by teh method proposed by Suzuki, et al (Eiyo to Shokuryo, Vol. 31, p. 395, 1978).

First, 1% aqueous lactoferrin solution in an amount of 1 l was dialyzed below at 4° C. for 30 hours with 0.1 mol citric acid solution containing 0.05% EDTA (pH 2.2) in an amount 20 times as large. The resultant product was further dialyzed with deionized water for 24 hours, and frozen and dried to obtain about 10 g apo lactoferrin.

Reference Example 2 (Preparation of EGF)

EGF was prepared as follows from human urine by the method of Cohen and Carpenter [S. Cohen and G. Carpenter: Proceedings of the National Academy of Science U.S.A., Vol. 72, p. 1317, 1975], the method of Savage and Happer [C. R. Jr. Savage and R. Happer: Analytical Biochemistry, Vol. 111, p. 195, 1981] and the method of Nishimuro, et al [S. Nishimuro, et al: Chemical and Pharmaceutical Bulletin, Vol. 33, p. 4037, 1985].

Acetic acid in an amount of 1 l was added to about 20 l human urine to make it acidic, and concentrated hydrochloric acid was added to adjust pH to 3.0 to 3.3. An ion exchange resin Bio-Rex70 (manufactured by Biorad Company) was adjusted with hydroacetic acid to a pH of 3.1, washed with 5% acetic acid, added to the above-mentioned urine, and stirred at 4° C. for 18 hours. After holding for two to four hours, supernatant liquid was removed, and the resin was washed with 0.01N hydrochloric acid, and EGF was eluted with 1M ammonium acetate (pH 8.0). The effluent liquid was frozen and dried, and the resultant dried product was dissolved in 50 ml distilled water. Then, 0.5 mg pepstein, 2 milli mol arginine and 200 mg bovine serum albumin (BSA) were added.

Ethanol in an amount of 1,500 ml was added to this solution, which was then stirred, held for 30 minutes, centrifuged at 1,000 xg for 20 minutes, and 15 ml of 2 mM (milli-mol/l) arginine were added to sedimentation. Then, pH was adjusted to 3.0 with hydrochloric acid, and centrifuged at 30,000 xg for 20 minutes to obtain supernatant liquid.

The above-mentioned supernatant liquid was passed through a column (4×14 cm) filled with DEAE cellulose equilibrated with 0.05% formic acid (manufactured by Wattman Company), and EGF in effluence not adhering to the column was collected. The effluent was frozen and dried, and the dried product was dissolved with 20 ml 0.05N hydrochloric acid, pH being adjusted to 1.5, and the resultant product was centrifuged at 3,000 xg for 30 minutes to obtain supernatant liquid.

A column (4×90 cm) filled with Bio-GelP-10 (manufactured by Biorad Company) was equilibrated with 0.05N hydrochloric acid. Elution was carried out at a flow rate of 42 ml per hour. While most of substances detected by UV absorption was eluted in 1.5 column volume, EGF was eluted after 1.7 column volume. Activity fractions were collected, pH being adjusted to 6.0 with ammonia water, and frozen and dried. The dried product was dissolved in 50 ml 0.04M ammonium acetate (pH 3.9), and concentrated to 5 ml through ultrafiltration.

A column (0.9×10 cm) filled with CM cellulose (manufactured by Wattman Company) was equilibrated with 0.04M ammonium acetate, and the above-mentioned concentrated liquid was applied to the colum. The Column was then washed with 0.04M ammonium acetate, and then eluted with 14 ml of 1M ammonium acetate. The effluent was frozen and dried. The dried product was then dissolved in 0.02M ammonium acetate (pH 5.3).

A column (0.9×10 cm) filled with DE-52 cellulose (manufactured by Wattman Company) was equilibrated with 0.02 mol ammonium acetate (pH: 5.3). Elution was carried out at flow rate of 8 ml per hour. After applying the above-mentioned solution, the column was washed with 0.02M ammonium acetate. Elution by a concentration gradient of 0.02 to 0.3 mol ammonium acetate gave three peaks (1 to 3). Major peaks of EGF activity are 1 and 3. EGF of about 150 to 250 µg was obtained.

Reference 3 (Preparation of Iron-saturated Lactoferrin)

Iron saturated lactoferrin was prepared as follows by the method of Suzuki, et al (Eiyo to Shokuryo, Vol. 31, p. 395, 1978) from commercially available bovine lactoferrin (Oleofina Company).

Then, 0.2 l of 0.1M sodium acetate solution containing 3 mM ferric chloride was added to 1 l of 1% aqueous solution of lactoferrin. The resultant solution was slowly stirred for an hour, dialyzed for 24 hours with deionized water, frozen and dried, to obtain about 10 g iron-saturated lactoferrin.

EXAMPLES

| Example 1 (preparation of tablets) | |
|---|---|
| Lactoferrin (Oleofina Company) | 50.0 (mg) |
| EGF by the same method as in Reference 2 | 0.01 |
| Crystalline cellulose | 170.0 |
| Corn starch | 66.0 |
| Talc | 11.0 |
| Magnesium stearate | 3.0 |

These raw materials were uniformly mixed by a conventional method at the above-mentioned ratios per tablet, granulated, dried, formed into tablets, and tablets were obtained. All the raw materials other than EGF were commercially available ones.

| Example 2 (preparation of powdery drug) | |
|---|---|
| Apo-lactoferrin based on the same method as in Reference 1 | 50.0 (g) |
| EGF based on the same method as in Reference 2 | 0.1 |
| Crystalline cellulose | 375.0 |
| Corn starch | 575.0 |

These raw materials were uniformly mixed, and 1,000 bags of powdery drug were prepared by a conventional method. All the raw materials other than apo-lactoferrin and EGF were commercially available ones.

| Example 3 (preparation of capsules) | |
|---|---|
| Iron saturated lactoferrin based on the same method as in Reference 3 | 10.0 (mg) |
| EGF based on the same method as in Reference 2 | 0.01 |
| lactose | 120.0 |
| Crystalline cellulose | 42.5 |
| Carboxymethylcellulose | 10.0 |
| Talc | 15.0 |
| Magnesium stearate | 2.5 |

These raw materials were uniformly mixed by a conventional method at the above-mentioned ratios, and prepared into capsule drug by means of a capsule filler. All the raw materials other than iron-saturated lactoferrin and EGF were commercially available ones.

| Example 4 (preparation of capsules) | |
|---|---|
| EGF based on the same method as in Reference 2 | 2.0 (mg) |
| Lactoferrin hydrolysis product based on the same method as in Test 2 | 20.0 (g) |
| Crystalline cellulose | 78.0 |
| Corn starch | 20.0 |
| lactose | 17.0 |
| Polyvinylpyrrolidone | 3.0 |

These raw materials were uniformly mixed, granulated by a conventional method, and put in 1,000 hard gelatine capsules to prepare capsule drug. All the raw materials other than lactoferrin hydrolysis product and EGF were commercially available ones.

| Example 5 (preparation of powdery drug) | |
|---|---|
| Lactoferrin (made by Oleofina Co.) | 25.0 (g) |
| Lactoferrin hydrolysis product based on the same method as in Test 2 | 25.0 |
| EGF based on the same method as in Reference 2 | 0.1 |
| Crystalline cellulose | 375.0 |
| Corn starch | 575.0 |

These raw materials were uniformly mixed, and 1,000 bags of powdery drug were prepared by a conventional method. All the raw materials other than lactoferrin hydrolysis product and EGF were commercially available ones.

EXAMPLE 6 (PREPARATION OF MODIFIED MILK POWDER)

Casein (manufactured by New Zealand Dairy Board) in an amount of 1.3 kg was dissolved in 15 l hot water, added with 5.6 kg lactose, 2.8 kg vegetable oil (manufactured by Nihol Yushi Company), vitamins and minerals, mixed, homogenized, and sterilized at 120° C. for three seconds. To this solution, a solution comprising 50 g commercially available lactoferrin (manufactured by Oleofina Company) and 50 mg EGF prepared by the same method as in the Reference 2 dissolved in 500 ml sterilized water. The mixture was uniformly mixed and spray-dried by a conventional method to obtain 10 kg modified milk powder.

EXAMPLE 7 (PREPARATION OF ENTERAL FEEDING)

Casein powder (manufactured by New Zealand Dairy Board) in an amount of 2 kg, 1.5 kg soy protein, and 1 kg lactoferrin hydrolysate prepared by the same method as in the Reference 2 were dissolved in 60 l hot water. To this solution, 12.5 kg hard digestible dextrine (manufactured by Matsutani Kagaku Kogyo Company), 3 kg vegetable oil (manufactured by Nihon Yushi Company), vitamins and minerals were added, homogenized, and adjusted into a total volume of 100 l and the mixture was sterilized at 150° C. for two seconds. Aqueous EGF solution prepared by dissolving 500 mg EGF prepared by the same method as in Reference 2 and passing through a sterilized filter was sterilizingly added to this mixed solution, mixed, and homogenized to obtain 100 kg liquid enteral feeding.

INDUSTRIAL APPLICABILITY

The digestive tract cells activating agent in the present invention is applicable as an drug ingredient for the manufacture of medical drugs, and also for the manufacture of various food products as a food additive.

What is claimed is:

1. A digestive tract cells activating agent which contains an epidermal growth factor and a hydrolysate of lactoferrin.

2. The digestive tract cells activating agent as claimed in claim 1, wherein the effective dose of administration for said epidermal growth factor is within a range of from 0.01 to 50 µg/kg of body weight per day for an adult.

3. The digestive tract cells activating agent as claimed in claim 1, wherein the effective dose of administration of said hydrolysate of lactoferrin is within a range of from 1 to 500 mg/kg of body weight per day for an adult.

4. A digestive tract cells activating agent which contains an epidermal growth factor and a lactoferrin.

5. The digestive tract cells activating agent as claimed in claim 4, wherein the effective does of administration of said epidermal growth factor is within a range of from 0.01 to 50 μg/kg of body weight per day for an adult.

6. The digestive tract cells activating agent as claimed in claim 4, wherein the effective dose of administration of said lactoferrin is within a range of from 1 to 500 mg/kg of body weight per day foran adult.

7. A digestive tract cells activating agent which contains an epidermal growth factor, and a mixture of a lactoferrin and a hydrolysate of lactoferrin.

8. The digestive tract cells activating agent as claimed in claim 7, wherein the effective dose of administration of said epidermal growth factor is within a range of from 0.01 to 50 μg/kg of body weight per day for an adult.

9. The digestive tract cells activating agent as claimed in claim 7, wherein the effective dose of administration of said mixture of the lactoferrin and the hydrolysate of lactoferin is within a range of from 1 to 500 mg/kg of body wight per day for an adult.

* * * * *